United States Patent

Clarke et al.

Patent Number: 5,982,484
Date of Patent: Nov. 9, 1999

[54] SAMPLE ANALYSIS USING LOW RESOLUTION RAMAN SPECTROSCOPY

[76] Inventors: Richard H. Clarke, 64 Pickney St., Boston, Mass. 02114; M. Edward Womble, 025 Coolidge Ave., #806, Watertown, Mass. 02172

[21] Appl. No.: 09/031,022

[22] Filed: Feb. 26, 1998

[51] Int. Cl.⁶ .............................. G01J 3/44; G01N 21/65
[52] U.S. Cl. ............................................................ 356/301
[58] Field of Search ............................................ 356/301

[56] References Cited

U.S. PATENT DOCUMENTS

| 5,139,334 | 8/1992 | Clarke | 356/301 |
| 5,370,790 | 12/1994 | Maggard et al. | 208/142 |
| 5,377,004 | 12/1994 | Owen et al. | 356/301 |
| 5,455,673 | 10/1995 | Alsmeyer et al. | 356/301 |
| 5,652,653 | 7/1997 | Alsmeyer et al. | 356/301 |

*Primary Examiner*—F. L. Evans
*Attorney, Agent, or Firm*—Thomas J. Engellenner; Nutter, McClennen & Fish, LLP

[57] ABSTRACT

The present invention provides an apparatus for measuring a property of a sample using low resolution Raman spectroscopy. The apparatus includes a multi-mode laser element, a wavelength dispersion element, a detector, and a processor. The multi-mode laser element irradiates a sample with laser radiation to produce a Raman spectrum. The collection element collects the radiation scattered from the molecules of the sample and transmits the scattered radiation to the dispersion element. The dispersion element disperses the scattered radiation into different wavelength components. The detection array detects the different wavelength components. A processor processes data from the detector array to identify a constituent or to measure a property of the sample. The apparatus preferably has a resolution of between 30 cm$^{-1}$ and 50 cm$^{-1}$. The resolution of the apparatus being determined in part by the spectral full width at half maximum of the multi-mode laser, and, in part, by the dispersion element.

15 Claims, 7 Drawing Sheets

SAMPLE ANALYSIS USING LOW RESOLUTION RAMAN SPECTROSCOPY

BACKGROUND OF THE INVENTION

The technical field of this invention is low resolution Raman spectroscopy and, in particular, the invention relates to analysis of a constituent or a property of a sample using low resolution Raman spectroscopy. The sample can be an liquid, such as an organic liquid. Alternatively, the sample can be a solid, such as a powdered drug.

It is known in the art that the chemical analysis of a liquid containing organic components either as the main constituent (e.g., hydrocarbon fuels, solvent mixtures, organic process streams) or as a contaminant (e.g., in aqueous solutions) can be based upon optical spectrum analysis of that liquid. The optical spectral analysis used can be near infrared (IR) analysis, despite its inherent low resolution. Near IR chemical analysis systems use inexpensive light sources and detectors. Advantageously, these systems also use optical fibers to deliver excitation radiation to the sample and to collect the resulting signal. In addition, chemometric analysis of broad spectral features improves the resolution of such near IR systems.

In contrast, mid IR analysis provides easily identifiable spectra for many samples of interest. Mid IR provides a "fingerprint" spectral region having sharp detail. The sharp detail of the fingerprint spectral region makes subsequent analysis easier.

Raman spectroscopy provides many of the advantages of near IR. Raman spectroscopy can also provide detailed spectral analysis, typical of mid IR spectroscopy, for organic systems, particularly for liquid organic systems. However, one drawback to Raman spectroscopy has been its expense relative to mid and near infrared systems.

A significant component of that expense is the laser system required to produce quality, high-resolution spectra. Even using a laser diode as the scattering source, the laser remains one of the major expenses in developing cost-effective Raman systems.

U.S. Pat. No. 5,139,334 issued to Clarke, and incorporated herein by reference, teaches a low resolution Raman spectral analysis system for determining properties related to the hydrocarbon content of fluids, in particular, the octane rating of gasoline. The system utilizes a laser Raman spectroscopic measurement of the hydrocarbon bands and relates specific band patterns to the property of interest. Different fuel properties are determined by a method that compares Raman-scattered light intensities over different wavelength ranges.

However, there remains a need for a low cost, portable, low resolution Raman spectroscopic system that does not depend on large and highly complex mechanical devices. Moreover, there exists a need for a low-resolution Raman spectroscopic system that provides a high intensity signal.

SUMMARY OF THE INVENTION

The present invention is directed to low resolution Raman spectroscopic systems for determining a constituent or a property of a sample. A system, according to the present invention, uses a multi-mode laser in making a Raman spectroscopic measurement of a sample. The system can further include a light collector and/or a light dispersion element as well as a detector to measure spectral patterns indicative of the constituent or property of interest. The presence of a constituent is determined by analyzing measured spectral data. Furthermore, a property can be measured by comparing Raman-scattered light intensities over different wavelength ranges.

One version of the present invention provides an apparatus for measuring a property of a sample using low resolution Raman spectroscopy. The apparatus includes a multi-mode laser element, a dispersion element, a collection element, a detection array, and a processor. The multi-mode laser element irradiates a sample with laser radiation to produce a Raman spectrum. The Raman spectrum is composed of scattered electromagnetic radiation characterized by a particular distribution of wavelengths. The Raman spectrum is a result of the scattering of the laser radiation as it passes through a sample. The laser radiation is scattered as it interacts with the rotational and vibrational motion of the molecules of the sample.

The collection element collects the radiation scattered from the molecules of the sample and transmits the scattered radiation to the dispersion element. The collection element can be an optical fiber. The collection fiber can have a first end positioned for collecting scattered radiation, and a second end positioned in selected proximity to the dispersion element. A notch filter can be coupled to the first end of the collection fiber for filtering the excitation source background.

The dispersion element distributes the scattered radiation into different wavelength components. The detection array detects the scattered radiation in different wevelength ranges, and a processor processes the detected array data to detect the presence and/or quantity of a constituent of or to measure a property of the sample.

The resolution of the apparatus is determined in part by the full width at half maximum (FWHM) of the spectral distribution of the multi-mode laser, and, in part, by the dispersion element. In one embodiment, the apparatus preferably has a resolution of between 10 $cm^{-1}$ and 100 $cm^{-1}$ and most preferably between 30 $cm^{-1}$ and 50 $cm^{-1}$.

The apparatus can further include an optical waveguide, such as an optical fiber, for transmitting the laser radiation from the multi-mode laser element to the sample. The fiber has a first end coupled to the multi-mode laser element, and a second end immersed in a liquid sample or in proximity to a solid sample.

The apparatus can further include a sample chamber adapted to receive a sample. The sample chamber can include a filter element for filtering out, from the sample chamber's interior, light having wavelengths substantially similar to the light being detected. The filter element can also provide high transmisivity of light in the visible spectrum to allow visual observation of the second end of the excitation fiber. Thus, an operator can insure that the second end of the excitation fiber is substantially centered in the sample.

According to a preferred embodiment, the multi-mode laser element produces laser radiation having a wavelength between about 700 nm and about 1 mm. The multi-mode laser preferably has a power between about 50 mw and about 1000 mw. One example of a multi-mode laser element for use with the present invention is a 785 nm GaAs laser diode. This GaAs multi-mode laser has a spectral distribution FWHM of approximately 30 $cm^{-1}$.

According to other features of the present invention, the processor can include a chemometric element for applying partial least square analysis to extract additional information from the Raman spectrum. The dispersion element can be a low resolution spectrometer. The low resolution spectrometer can be a monochromator. The detection array can be a diode array detector. Alternatively, the detection array can be a noncooled charged coupled device detector. The collection fiber can include a fiberoptic immersion probe.

In one aspect of this invention, systems are disclosed which correlate the laser Raman spectral features of a hydrocarbon mixture. The low resolution Raman Spectroscopy (LRRS) approach relies on the fact that only certain spectral features need to be resolved to identify the components in an organic liquid sample. For example, in a toluene and xylene mixture a band at 1000 cm-1 indicates the presence of an aromatic ring. The aromatic ring compounds can be distinguished by a 728 cm-1 band (xylene) and a 785 cm-1 band (toluene). In a toulene/xylene mixture spectra the toluene/xylene ratio is clearly determined using a LRRS system capable of measuring these two bands, despite the fact that the two usual high-resolution Raman features at 1002 cm-1 (toluene) and 1013 cm-1 (xylene) may not be resolved at all in the LRRS spectrum.

This invention is particularly useful in that it can provide a quick and reliable determination of a number of fluid properties through a single spectral measurement on microliter samples. The present invention thus permits a chemical analysis to be determined without resort to an elaborate, multi-step analysis procedure requiring large quantities of sample.

In one illustrated embodiment of the present invention, a low resolution, portable Raman spectrometer is disclosed. It can incorporate an immersible fiberoptic sensing probe, connected to a multi-mode laser diode, as the source of scattering light, a low-resolution dispersion element and a diode array for spectral pattern detection. The diode array output can be analyzed through an integrated microprocessor system configured to provide output in the form of specific mixture properties. The use of optical fibers, multi-mode laser diodes, a low-resolution dispersion element and diode arrays detectors allows the system to be small, portable, field-reliable, and sensitive to small amounts of constituents of interest. Furthermore, this configuration can provide an inexpensive device that would permit the continuous testing of the chemical components of an organic liquid.

The invention can also be used to monitor the properties of other hydrocarbon-containing fluids, such as lubricating oils and the like. Typically, lubricating oils will experience changes in their hydrocarbon composition over time, and such changes are indicative of loss of lubricating efficiency. The apparatus of the present invention can be readily applied to monitor such changes.

The invention will next be described in connection with an illustrated embodiment. However, it should be clear that various changes, additions and subtractions can be made without departing from the spirit or the scope of the invention.

DETAILED DESCRIPTION

Figure 1:
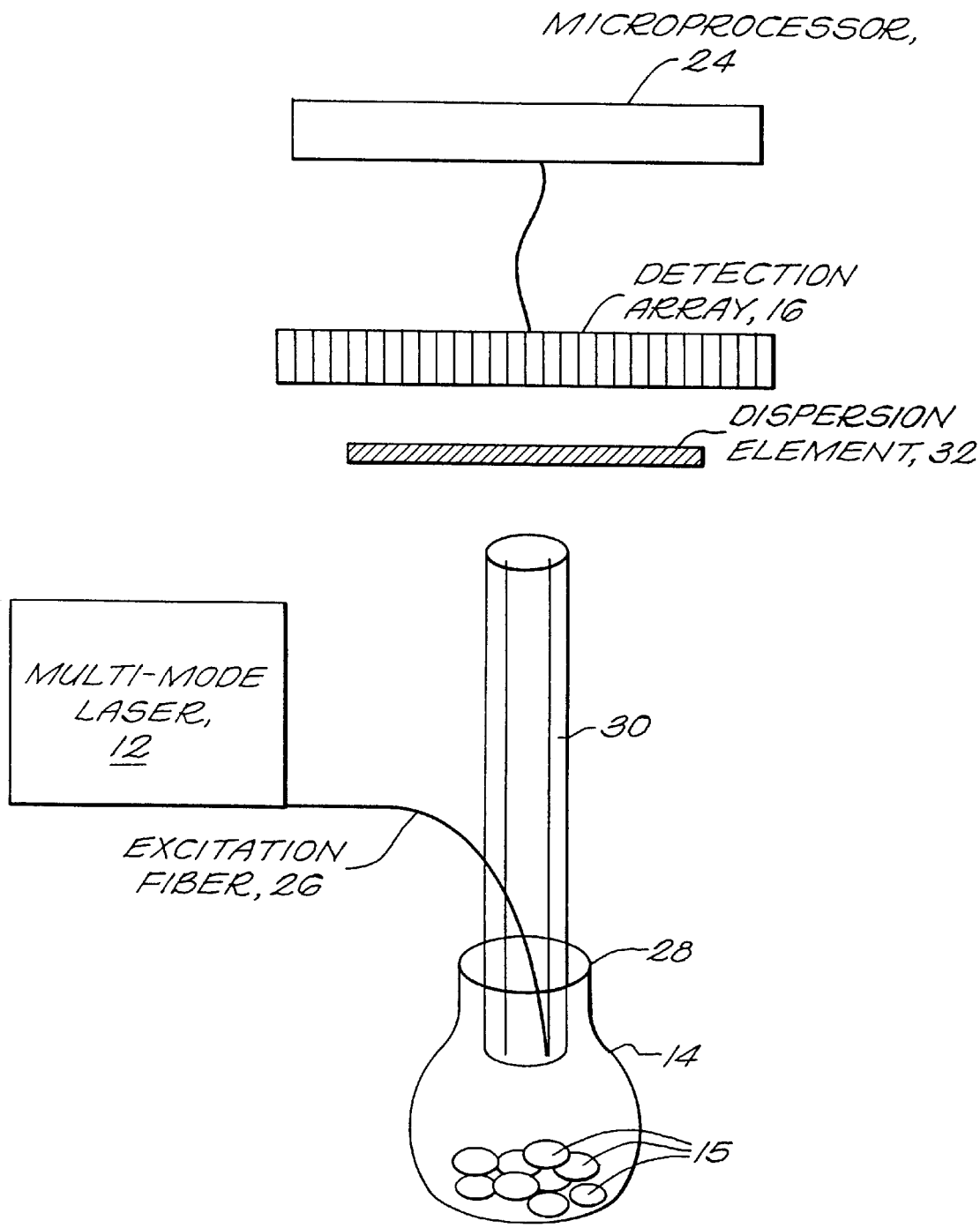
FIG. 1 is a block diagram of a portable fluid-property sensor system according to the invention.

FIG. 1 is a block diagram of a sensor system 10A that is particularly well-suited for sampling from a remote location and the measurement of several liquid properties at once. System 10 includes a multi-mode laser source 12 connected to an excitation optical fiber 26 that carries the laser light to a sample chamber 14 that lies at a remote location. A Powertechnology multi-mode laser HPM 500 (785–1000) F1X12, available from Powertechnology, Little Rock, Ark., can be used as the multi-mode laser. The sample chamber 14 can have at least one porous wall or surface 28. The sample chamber 14 can further include reflective elements 15 which enhance the collection of Raman scattered light from the sample. The Raman scattered light is collected by a flexible optical fiber bundle 30 that is also optically coupled to the sample chamber 14. The fiber bundle 30 can be coated to reject the wavelength of the laser source light. The Raman scattered light travels through the fiber bundle 30 into a low-resolution dispersion device 32, that serves to disperse the scattered light into its different wavelength components. The dispersed scattered light is detected by photodetector array 16 that, in this case, consists of a photodiode array or a charged-coupled device (CCD) array.

Specific spectral bands of interest are measured at low resolution to obtain the integrated band intensities. These bands can be narrow ones. For example, a first band centered around the 728 $cm^{-1}$ peak can be chosen ranging from about 713 $cm^{-1}$ to about 743 $cm^{-1}$ xylene, and a second band from about 770 $cm^{-1}$ to about 800 $cm^{-1}$ bracketing the 785 $cm^{-1}$ toulene peak can be chosen as the second range.

Again, with reference to FIG. 1, the resolving power of the dispersion device 32 determines the position of specific wavelengths in the diode array in such a way that the signal from a particular diode in the array will typically correspond to the same (or a similar) narrow range of wavelengths. This combination of the low-resolution dispersion device 32 and the diode array photodetector 16 thus form a Raman spectrometer. The microprocessor 24 selects a particular diode (or diodes) of the array 16 according to the property to be measured. The integrated signals lying in the two ranges can be arithmetically divided to form intensity ratios. The microprocessor 24 compares these ratios with known values or a correlating function to obtain an estimate of the chemical constituent or property of interest.

Advances in the field of solid state lasers have introduced several important laser sources into Raman analysis. For high-resolution Raman systems the laser linewidth must be severely controlled, often adding to the cost of the excitation source and the system as a whole. For low resolution Raman spectroscopy (LRRS), however, the strategy of relinquishing resolution details in favor of emphasizing essential identifying spectral features, allows the use of a low cost, high energy multi-mode laser and a low resolution dispersion element. A multi-mode laser which can be used with a LRRS system, according to one embodiment of the present invention, is available in higher power ranges (between 50 mw and 1000 mw) than is available with a traditional single mode laser (<150 milliwatts). The higher power of a multi-mode laser increases the amount of scattered radiation available to the spectrometer system. The sensitivity of the LRRS system increases at least linearly with laser power.

A low resolution dispersion element can provide greater transmission of scattered radiation to the detector array. For example, a low resolution diffraction grating with wider slits than a typical diffraction grating can be used, providing greater transmission of incident scattered radiation to the detector array. Thus, the combination of a low cost, high energy multi-mode laser and a low loss dispersion element provides an inexpensive LRRS system that provides a high intensity signal.

In a typical LRRS application the need for feature separation is much like that encountered in mid-IR spectroscopy. The use of multi-mode lasers causes a degradation in the resolution of the spectrometer. The resolution of the LRRS system decreases primarily because the width of the laser line used to excite the sample is much larger with multi-mode lasers than it is with a single mode laser. A multi-mode laser has a linewidth of 2–3 nanometer. In comparison, a single mode laser has a linewidth of a fraction of a nanometer. However, one rarely requires single wavenumber resolution to find a spectral fingerprint feature that allows identification and quantification of a sample under analysis. Similarly, in LRRS, since the approach uses fundamental frequencies, even if not fully resolved, in the spectral analysis, a broader band laser source may suffice for the Raman analysis. In this case inexpensive, multi-mode solid state laser sources are both sufficient for the task and cost effective, and high power.

Since a Raman measurement is the difference in wavelength between the scattered light and the excitation line, an excitation line that has a larger spectral FWHM causes a proportional loss of resolution in the resulting Raman measurement. However, this reduction of resolution is offset by the advantages of lower cost and increased signal intensity. The increased signal intensity is a result of a higher energy laser source and wider slits in the diffraction grating allowing more light into the detector array. Since the spectrometer system resolution has been substantially reduced by the use of a multi-mode laser, the width of the slits can be increased with negligible effect on resolution. In addition, a CCD detector array can be matched to the lower resolution laser source and the dispersion element by reducing the number of elements in the array. For example, instead of 4096 array elements, one can use 2048 larger elements.

Thus, a complete LRRS spectroscopic system can consist of an inexpensive multi-mode laser diode operating at a higher power (between 50 mw and 1000 mw output) than traditional single-mode Raman sources and a low resolution monochromator matched to a simple CCD detector, with Rayleigh filtering provided by notch filters capable of removing the excitation source background.

Various organic liquids were tested with several combinations of solid state lasers and low resolution monochromators and the results are reported below. The laser sources were all in the range of 785–810 nm, both single mode and multi-mode diodes with powers ranging from 50–500 mw. The monochromators were the Ocean Optics S-1000 and S-2000, one with diode array detector (S-1000) and one with a noncooled CCD detector (S-2000), commercially available from Ocean Optics in Dunedin, Fla. Optical filters were used to eliminate the Rayleigh line. A simple fiberoptic immersion probe (Visionex, Inc., Warner Robins, Ga.) was used to collect the spectra.

In one test, the Applicants used a 500 mw 785 multi-mode laser diode as the excitation source, coupled to a S-2000 monochromator, to provide its Raman signals. This Raman system was used with the Visionex fiberoptic probe for sample collection.

The Applicants examined a series of organic liquid samples using the LRRS configuration described above.

EXAMPLE 1-Alcohol mixture

A mixed solution of alcohols was prepared from 33% ethyl alcohol, 33% isopropyl alcohol, and 33% t-butyl alcohol (Aldrich Chemicals). These alcohols were selected because of their signature $C_n$-O skeletal vibrational band in the Raman spectrum. With the low resolution Raman system described above and an integration time of 60 seconds, the spectrum shown in FIG. 2 was obtained for the mixture.

Figure 2:
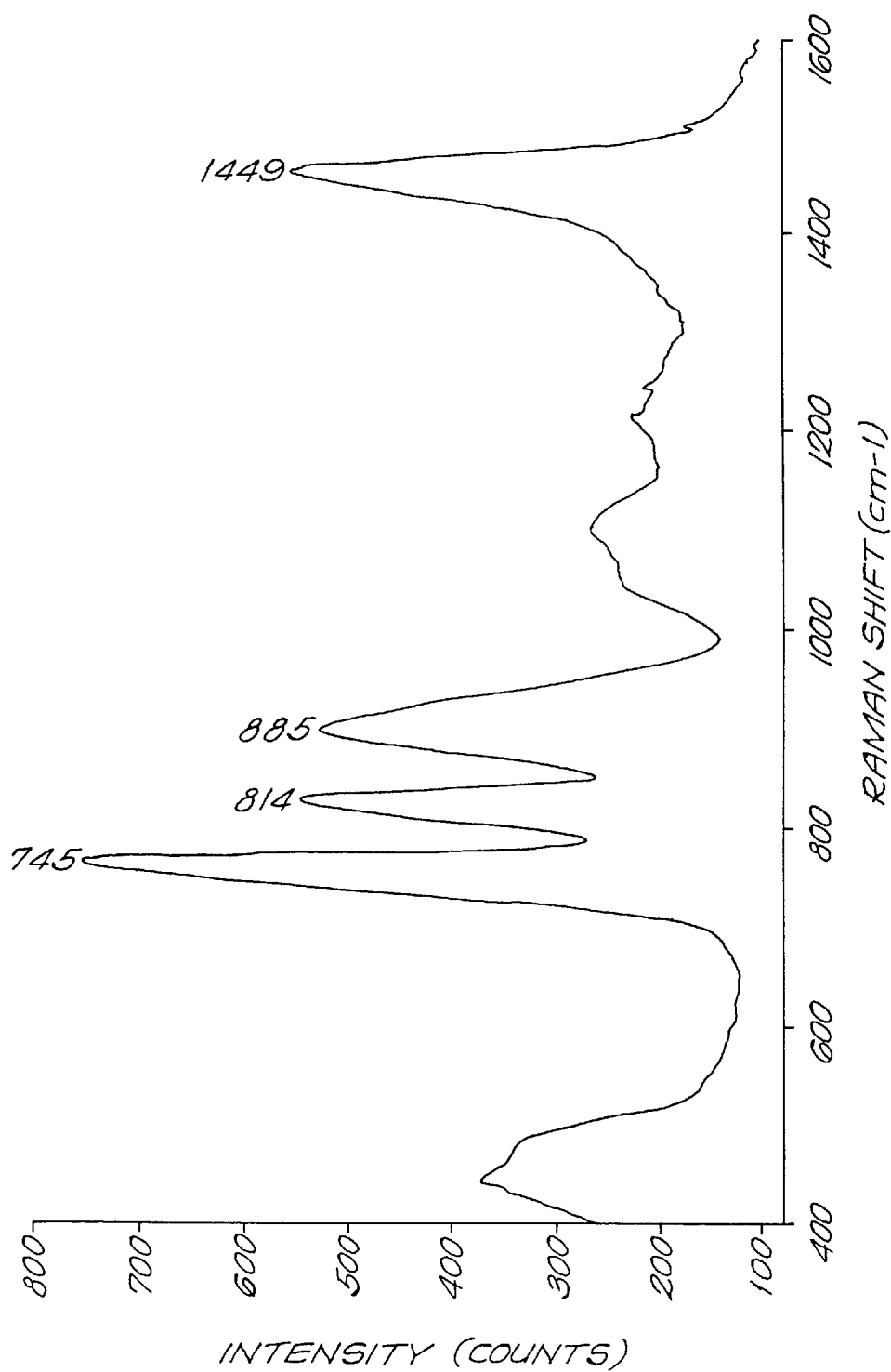
FIG. 2 is a spectrum obtained from a 1:1:1 mixture of ethyl alcohol, isopropyl alcohol, and t-butyl alcohol using a system of the type shown in FIG. 1.

FIG. 2 shows the characteristic $C_n$-O Raman band for each alcohol clearly resolved in the LRRS system. The band at 745 cm-1 corresponds to the $C_4$-O skeletal vibration of a tertiary alcohol (t-butyl), the band at 815 cm-1 to the $C_3$-O skeletal stretch of a secondary alcohol (isopropyl), and the 886 cm-1 peak to the $C_2$-O skeletal mode of a primary alcohol (ethanol).

EXAMPLE 2-Aromatic/aliphatic mixture

Figure 7:
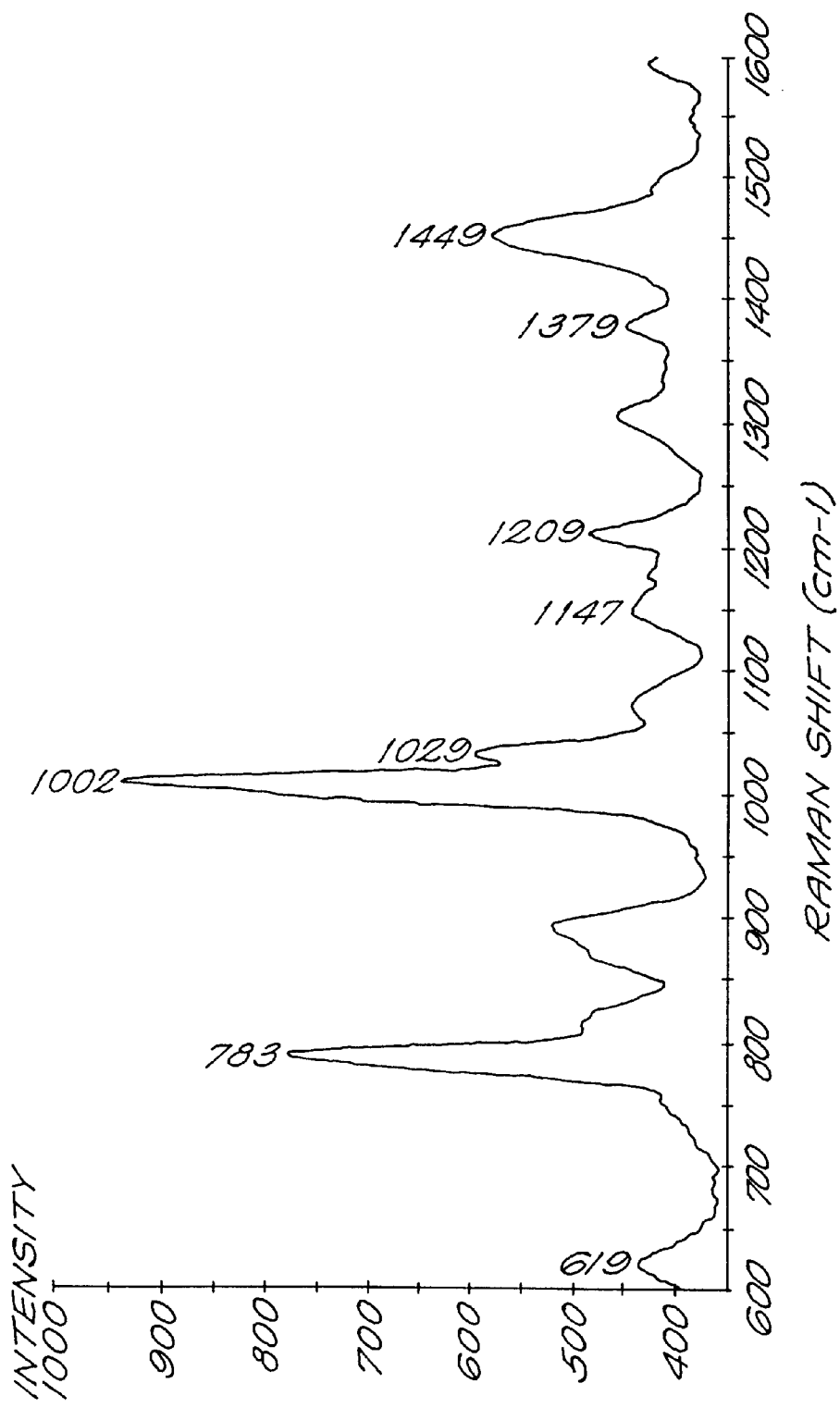
FIG. 7 is a spectrum obtained from a 1:1 mixture of toluene and n-haxane using a system of the type shown in FIG. 1.

Toluene and n-hexane (J. T. Baker) were mixed as received in the ratio 1:1 by volume. Five milliliters of the solution was placed in an amber glass cuvette and the immersion probe of the R-2000 used to acquire the Raman spectrum. The full Raman spectrum of the mixture solution is shown in FIG. 7.

The most prominent band, occurring at 1002 cm-1, arose from the symmetrical (trigonal) ring breathing mode of a mono-substituted benzene. The small shoulder to this band at 1024 cm-1 is associated with the in-plane CH deformation in toluene. The 786 cm-1 peak corresponded to a monosubstituted benzene ring vibration. The aliphatic component of the solution was represented by the band at 1449 cm-1, the CH2, CH3 deformation mode that characterizes n-alkanes.

EXAMPLE 3-BTEX mixture

Figure 3:
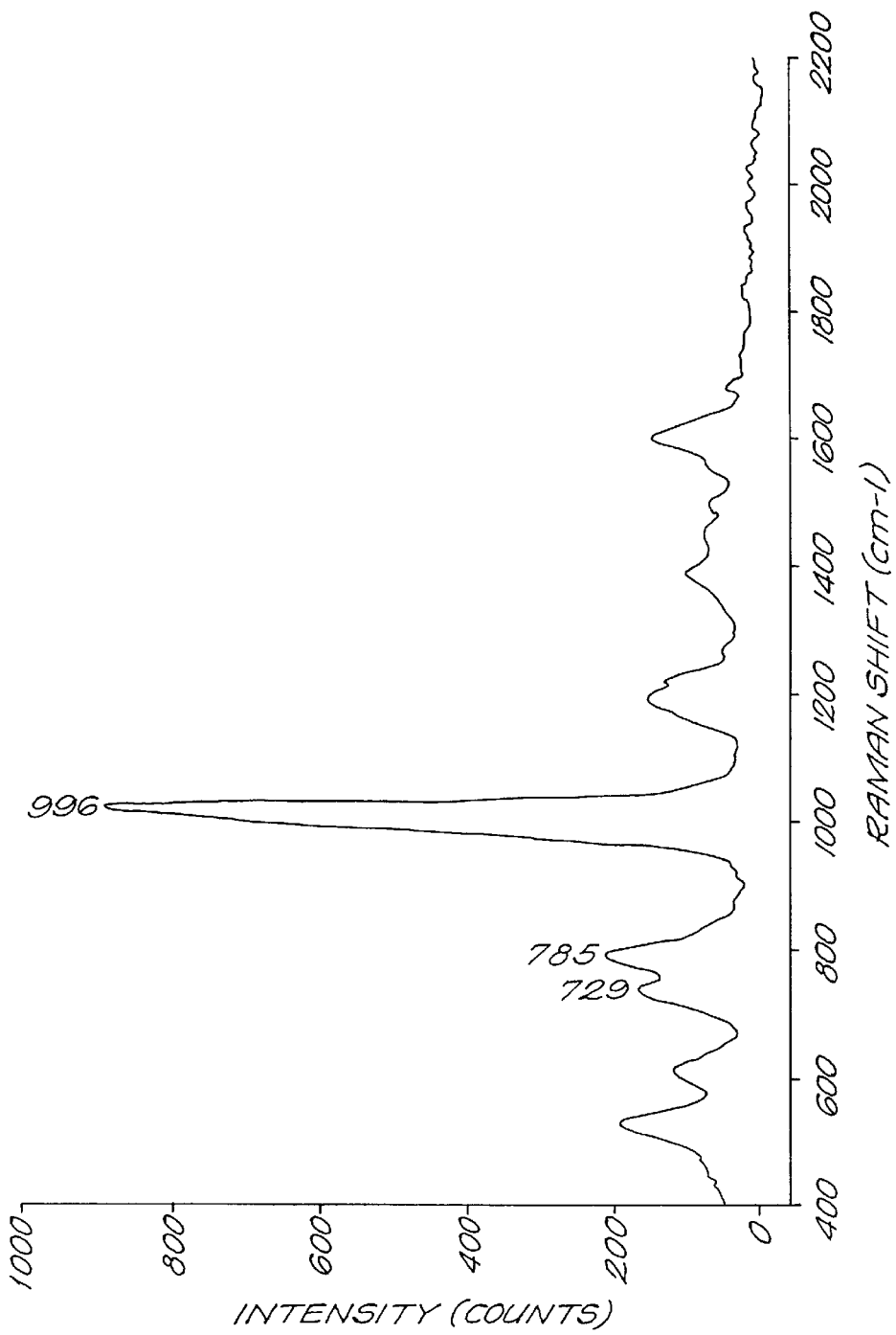
FIG. 3 is a spectrum obtained from a 1:1:1 mixture of benzene, toulene, and xylene using a system of the type shown in FIG. 1.

Benzene (E.M. Science), toluene (J. T. Baker), and xylene (mixture of three isomers, J. T. Baker) were mixed as received at room temperature in 1:1:1 ratio by volume. A Raman spectrum of this "BTEX" mixture was recorded on the R-2000 system with an integration time of 60 seconds, with the laser power set at 420 milliwatts; the spectrum is shown in FIG. 3.

In the mixture the strong band at ~1000 cm-1 indicated the presence of at least one monoaromatic ring. The ring systems were further identified through the peaks at 725 cm-1 (xylenes) and 786 cm-1 (toluene). All such peaks were readily resolved using any laser system, single or multi-mode, for the excitation source.

The LRRS approach relies on the fact that only certain spectral features need to be resolved to identify the components in an organic liquid sample. This point is best appreciated in the examples of aromatic and aliphatic mixtures, such as the BTEX of FIG. 3 and hydrocarbon fuel spectra in FIGS. 4–6. In the BTEX mixture of FIG. 3, the band at 1000 cm-1 indicated the presence of the aromatic ring which is then further differentiated by the 728 cm-1 band (xylene) and the 785 cm-1 band (toluene), Note that in this spectrum the toluene/xylene ratio was clearly determined, despite the fact that the two usual high-resolution Raman features at 1002 cm-1 (toluene) and 1013 cm-1 (xylene) are not resolved at all in the LRRS spectrum.

EXAMPLE 4-Gasolines

Figure 4:
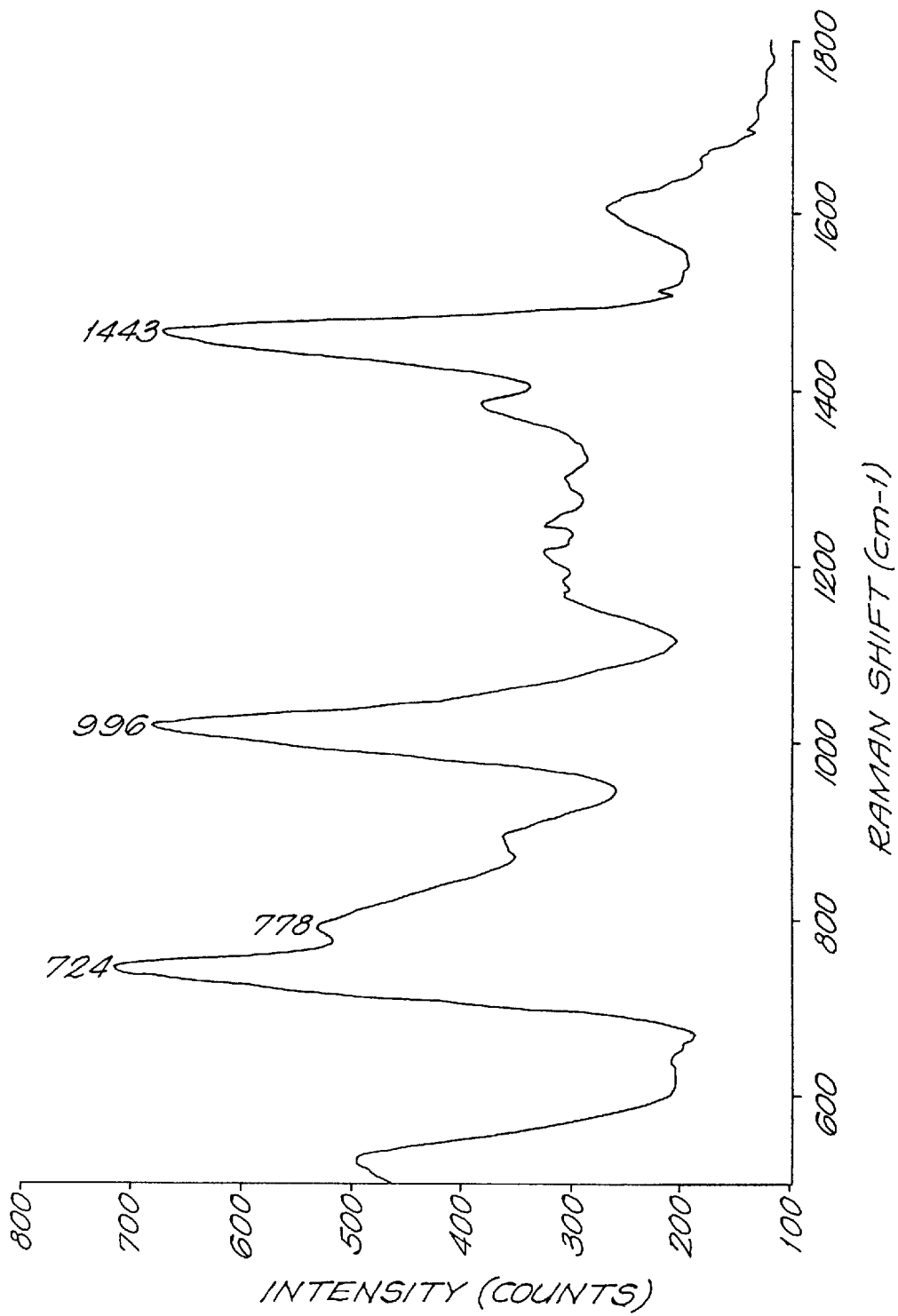
FIG. 4 is a spectrum obtained from 87 octane gasoline using a system of the type shown in FIG. 1.
Figure 5:
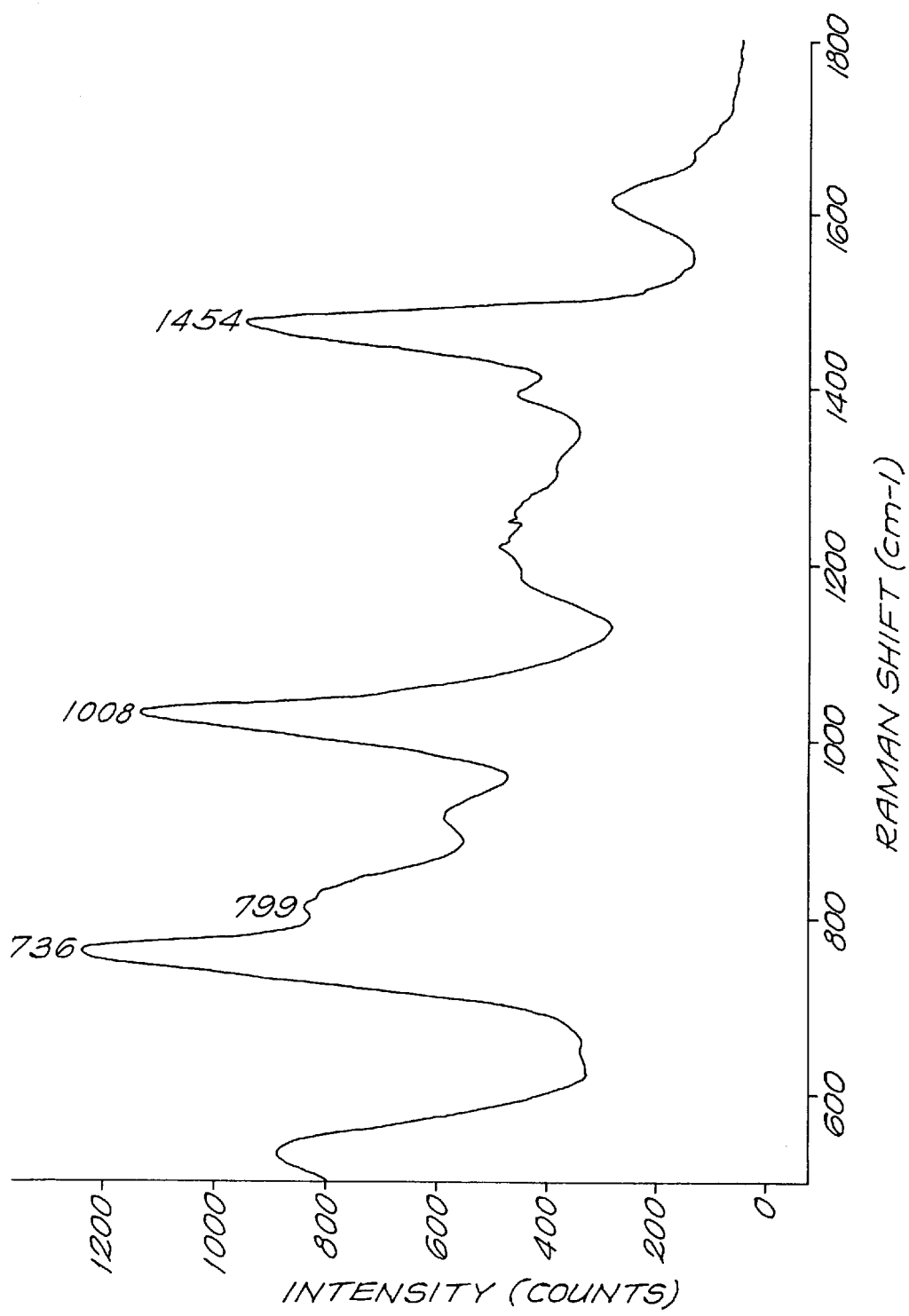
FIG. 5 is a spectrum obtained from 90 octane gasoline using a system of the type shown in FIG. 1.
Figure 6:
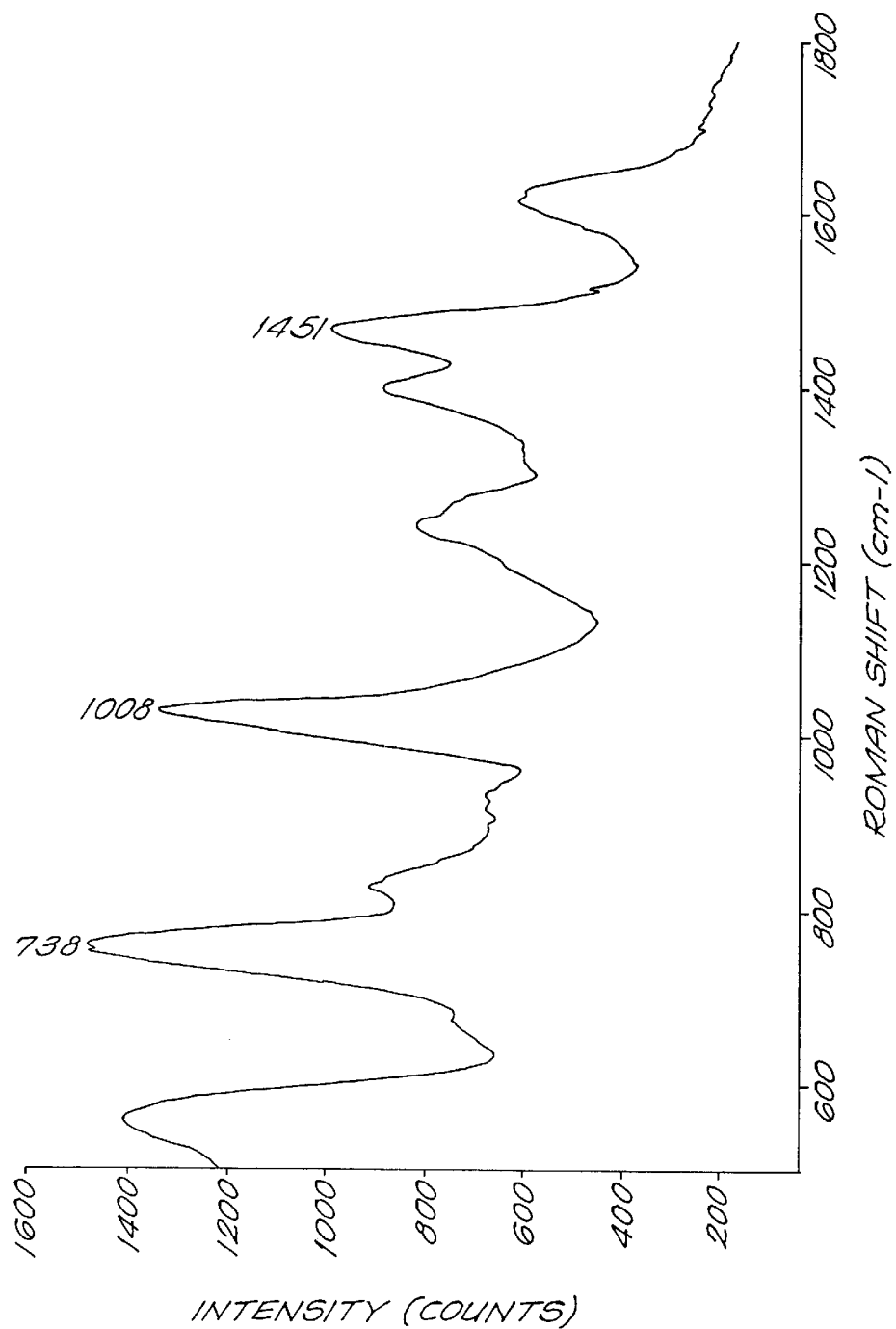
FIG. 6 is a spectrum obtained from 93 octane gasoline using a system of the type shown in FIG. 1.

The examples of hydrocarbon fuels further illustrate the capability of LRRS in sample identification and characterization. In FIGS. 4, 5, and 6, the LRRS spectra of three grades of gasoline are depicted. These spectra were obtained with a 60 second integration time. In many cases aromatics are blended into gasolines to enhance their octane rating. Even in the LRRS spectra of these fuels, one can clearly see the aromatic fraction in the 1000 cm-1 region fully distinguishable from the olefinic background of the fuels indicated by the 1450 cm-1 band. The relative heights of the 1000 cm-1 and 1450 cm-1 band are characteristic of the aromatic fraction of the fuel blend. Examining the LRRS spectra of the 87, 90, and 93 octane samples of FIGS. 4, 5, and 6, respectively, one can see the heights of the 1000 cm-1 bands increasing in the aromatic region as the octane rating of the fuel increases.

Again, in the case of the alcohol mixture, the Raman features important in the differentiation of the components are recovered in the LRRS peaks. Even in the case of deliberately lowering the resolution conditions (through use of the broader laser source), the identification of the three alcohols, i.e., ethyl, isopropyl, and t-butyl, is still evident. Moreover, the relative peak heights readily provide the concentration ratios of the components in the mixture at the resolution level provided.

The LRRS system used in this example might not be of sufficiently high resolution to provide the required analysis for certain samples. However, as in the case of mid-IR, it is not always necessary to have high spectroscopic resolution to arrive at an analytical determination of interest. As in the case of near-IR, lower resolution may be preferred when considering the system's signal intensity and cost.

The features of the displayed LRRS examples are clearly defined only to an arbitrary resolution standard. Further lowering of the LRRS resolution threshold can support a more detailed analysis (e.g., a filter-based Raman system).

It will thus be seen that the objects set forth above, among those made apparent from the preceding description, are attained. Various changes may be made in the above described embodiments without departing from the spirit or scope of the invention; it being intended that all matter contained in the above description and shown in the accompanying drawings be interpreted as illustrative and not in a limiting sense. It is also to be understood that the following claims are intended to cover all generic and specific features of the invention described herein, and all statements of the scope of the invention which as a matter of language might be said to fall therebetween.

Having described the invention, what is claimed as new and sought to be secured by letters patent is:

We claim:

1. An apparatus for measuring a property of a sample using low resolution Raman spectroscopy, the apparatus comprising:

multi-mode laser for irradiating a sample with laser radiation having a line width of at least 2 nanometers to produce a Raman spectrum consisting of scattered electromagnetic radiation, a low-resolution dispersion element positioned to receive and separate said scattered radiation into different wavelength components, said components being separated by a resolution ranging from about 10 $cm^{-1}$ to about 100 $cm^{-1}$, a detection array, optically aligned with the dispersion element for detecting at least some of the wavelength components of the scattered light, and a processor for processing data from the detector array to measure a property of the sample.

2. The apparatus of claim 1, wherein the apparatus further comprises an excitation fiber for transmitting said laser radiation from said multi-mode laser to said sample, said excitation fiber having a first end coupled to said multi-mode laser, and a second end positioned for interaction with said sample.

3. The apparatus of claim 2, wherein the apparatus further comprises a sample chamber adapted to receive a sample.

4. The apparatus of claim 3, wherein the sample chamber comprises a filter for excluding, from said sample chamber's interior, radiation having wavelengths substantially similar to radiation being detected.

5. The apparatus of claim 1, wherein the multi-mode laser produces laser radiation having a wavelength between about 700 nm and about 1 mm.

6. The apparatus of claim 1, wherein the multi-mode laser comprises a 785 nm GaAs laser diode.

7. The apparatus of claim 1, wherein the multi-mode laser has a full width at half maximum of 30 $cm^{-1}$.

8. The apparatus of claim 1, wherein the multi-mode laser has a power between about 50 mw and about 1000 mw.

9. The apparatus of claim 1, wherein the processor includes a chemometric means for applying partial least square analysis for extracting information from said Raman spectrum.

10. The apparatus of claim 1, wherein said dispersion element is a low resolution diffraction grating.

11. The apparatus of claim 1, wherein said dispersion element comprises a monochromator.

12. The apparatus of claim 1, wherein said detection array comprises a diode array detector.

13. The apparatus of claim 1, wherein said detection array comprises a charged coupled device detector.

14. The apparatus of claim 1, wherein said apparatus further comprises a collection fiber for collecting light scattered from a sample.

15. The apparatus of claim 1, wherein said apparatus has a resolution of between 30 $cm^{-1}$ and 50 $cm^{-1}$, said resolution of said apparatus being determined in part by said multi-mode laser and, in part, by said dispersion element.

* * * * *